United States Patent
Straguzzi et al.

(10) Patent No.: US 6,974,843 B2
(45) Date of Patent: Dec. 13, 2005

(54) COGENERATION OF ORGANIC COMPOUNDS WITH SYNTHESIS GAS BY CATALYTIC PARTIAL OXIDATION

(75) Inventors: Gloria I. Straguzzi, Ponca City, OK (US); Mary E. Wolf, Ponca City, OK (US); Harold A. Wright, Ponca City, OK (US)

(73) Assignee: Conoco Phillips Company, Houston, TX (US)

( * ) Notice: Subject to any disclaimer, the term of this patent is extended or adjusted under 35 U.S.C. 154(b) by 154 days.

(21) Appl. No.: 10/405,288

(22) Filed: Apr. 2, 2003

(65) Prior Publication Data

US 2004/0198844 A1 Oct. 7, 2004

(51) Int. Cl.[7] .................... C07C 27/00; C07C 1/02; C01B 31/18; C01B 3/26
(52) U.S. Cl. .................. 518/703; 518/702; 423/418.2; 423/651; 252/373
(58) Field of Search ................ 518/702, 703; 423/418.2, 651; 252/373

(56) References Cited

U.S. PATENT DOCUMENTS

| | | |
|---|---|---|
| 4,760,210 A | 7/1988 | Sweeney |
| 5,023,276 A | 6/1991 | Yarrington et al. |
| 5,720,901 A | 2/1998 | De Jong et al. |
| 5,856,585 A | 1/1999 | Sanfilippo et al. .......... 568/470 |
| 6,333,294 B1 | 12/2001 | Chao et al. .................. 502/325 |
| 6,402,989 B1 | 6/2002 | Gaffney ....................... 252/373 |
| 2002/0115730 A1 | 8/2002 | Allison et al. |

FOREIGN PATENT DOCUMENTS

WO   WO02/20395   3/2002   ............. C01B/3/38

OTHER PUBLICATIONS

Form PCT/ISA/220, *Notification of Transmittal of the International Search Report and the Written Opinion of the International Searching Authority, or the Declaration*, for PCT/US04/09665, date Feb. 28, 2005.

Harold Gunardson, *Industrial Gases In Petrochemical Processing: Chapter 2, Synthesis Gas Manufacture*, Marcel Dekker, Inc. (1998) pp. 41–80.

D.W. Larkin et al., *The direct partial oxidation of methane to organic oxgenates using a dielectric barrier discharge reactor as a catalytic reactor analog*, Catalysis Today (2001) pp. 199–210.

Primary Examiner—J. Parsa

(57) ABSTRACT

Disclosed herein are methods and apparatuses for cogenerating organic compounds (e.g., benzene, toluene, xylene, formate, acetate, propionate, butyrate, $C_1$–$C_4$ acids, $C_1$–$C_4$ alcohols, methanol, naphthalene, acenaphthylene, fluorene, phenanthrene, anthracene, fluoranthene, and pyrene) along with synthesis gas in a synthesis gas reactor, preferably a catalytic partial oxidation reactor.

19 Claims, 1 Drawing Sheet

COGENERATION OF ORGANIC COMPOUNDS WITH SYNTHESIS GAS BY CATALYTIC PARTIAL OXIDATION

CROSS-REFERENCE TO RELATED APPLICATIONS

Not applicable.

STATEMENT REGARDING FEDERALLY SPONSORED RESEARCH

Not applicable.

TECHNICAL FIELD OF THE INVENTION

The present invention relates to processes and apparatus for the cogeneration of synthesis gas and organic compounds and to the synthesis gas and organic compounds produced by the processes and apparatus.

BACKGROUND OF THE INVENTION

Natural gas, found in deposits in the earth, is an abundant energy resource. For example, natural gas commonly serves as a fuel for power generation or a fuel for domestic use. The process of obtaining natural gas from an earth formation typically includes drilling a well into the formation. Wells that provide natural gas are often remote from locations with a demand for the consumption of the natural gas.

Thus, natural gas is conventionally transported large distances from the wellhead to commercial destinations in pipelines. This transportation presents technological challenges due in part to the relatively large volume occupied by gaseous natural gas. Therefore, the process of transporting natural gas typically includes chilling and/or pressurizing the natural gas in order to liquefy it. However, the expenditures associated with liquefaction are generally very high and liquefaction is not economical for formations containing small amounts of natural gas.

Formations that include small amounts of natural gas may be merely small natural gas fields or may include primarily oil, with the natural gas being a byproduct of oil production ("associated gas"). In the past, associated gas has typically been flared. However, current environmental concerns and regulations often discourage or prohibit this practice.

Further, naturally occurring sources of crude oil used for liquid fuels such as gasoline, jet fuel, kerosene, and diesel have been decreasing and supplies are not expected to meet demand in the coming years. Fuels that are liquid under standard atmospheric conditions have the advantage that they can be transported more easily in a pipeline than natural gas, since they do not require the energy, equipment, and expense required for liquefaction.

Thus, for all of the above-described reasons, there has been interest in developing technologies for converting natural gas to more readily transportable liquid fuels. One method for converting natural gas to liquid fuels involves two sequential chemical transformations. In the first transformation, natural gas or methane, the major chemical component of natural gas, is reacted to form a mixture of CO and $H_2$ ("synthesis gas" or "syngas"). This syngas generation usually occurs either by dry reforming, steam reforming, or partial oxidation, respective examples of which are set forth below for methane:

$$CH_4 + CO_2 \rightarrow 2CO + 2H_2 \qquad (1)$$

$$CH_4 + H_2O \rightarrow CO + 3H_2 \qquad (2)$$

$$CH_4 + \tfrac{1}{2}O_2 \rightarrow CO + 2H_2 \qquad (3)$$

Reactions (1) and (2) are endothermic and reaction (3) is exothermic. Examples of syngas processes are disclosed in U.S. Pat. No. 6,402,989 to Gaffney and Gunardson, Harold, "Industrial Gases in Petrochemical Processing" 41–80 (1998), both incorporated herein by reference.

In the second transformation, known generically as hydrocarbon synthesis (e.g., the Fischer-Tropsch process), carbon monoxide reacts with hydrogen to form organic molecules containing carbon and hydrogen. Those molecules containing only carbon and hydrogen are known as hydrocarbons. Hydrocarbons having singly bonded carbons are known as paraffins and are particularly desirable as the basis of synthetic diesel fuel. An example of a Fischer-Tropsch process is disclosed in U.S. Pat. No. 6,333,294 to Chao et al., incorporated herein by reference.

Typically, a Fischer-Tropsch product stream contains hydrocarbons having a range of numbers of carbon atoms, and thus having a range of weights. Thus, the product produced by conversion of natural gas, often called "syncrude," commonly contains a range of hydrocarbons including light gases, gases, light naphtha, naphtha, kerosene, diesel, heavy diesel, heavy oils, waxes, and heavy waxes. These cuts are approximate and there is some degree of overlapping of components in each range.

SUMMARY OF THE DISCLOSURE

Surprisingly, it has been discovered that, depending on the syngas reactor conditions, secondary products, such as, by way of example only, oxygenated organic compounds like organic acids, salts, and alcohols comprising 1 to 4 carbon atoms, aromatic and polyaromatic compounds like benzene, toluene, and anthracene Disclosed herein are apparatus, methods, and products relating to the cogeneration of secondary products (e.g., benzene, toluene, xylene, organic acids and salts comprising 1 to 4 carbon atoms such as formate, acetate, propionate, butyrate, methanol, naphthalene, acenaphthylene, fluorene, phenanthrene, anthracene, fluoranthene, and pyrene) along with synthesis gas in a catalytic partial oxidation reactor.

BRIEF DESCRIPTION OF THE DRAWING

For a more detailed description of the present invention, reference will now be made to the accompanying FIGURE.

DETAILED DESCRIPTION OF THE PREFERRED EMBODIMENTS

Figure 1:
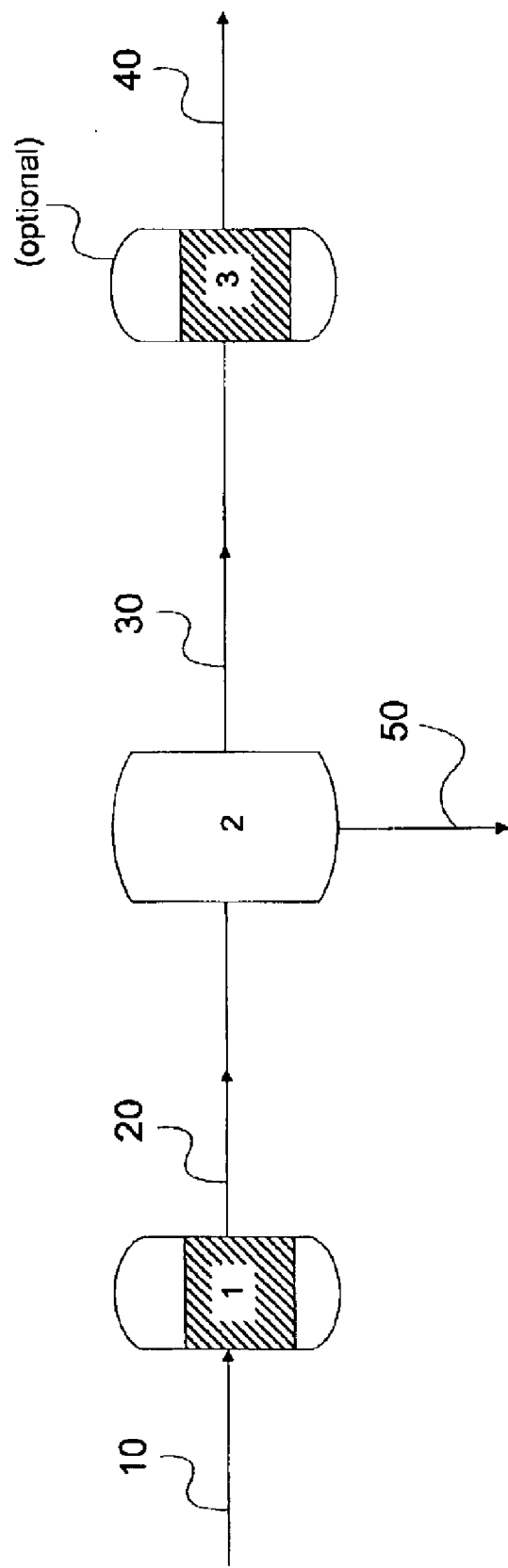
FIG. 1 is a schematic drawing of a preferred reactor scheme in accordance with the present invention.

Referring to FIG. 1, there is shown feedstream 10, reactor 1, syngas stream 20, separator 2, separated syngas stream 30, outlet stream 50, optional synthesis reactor 3, and product stream 40.

In operation in the reactor scheme according to FIG. 1, feedstream 10 comprises a hydrocarbon-containing gas and an oxygen-containing gas, preferably, natural gas or methane and substantially pure molecular oxygen. Feedstream 10 is fed into reactor 1 at conditions effective to partially oxidize at least a portion of the feedstream to synthesis gas (CO and $H_2$) and convert at least a portion of the feedstream to secondary products, such as, by way of example only, methanol, organic acids or salts, or benzene. Feedstream 10 preferably has a molar ratio of hydrocarbons to oxygen in the range of about 1.5:1 to about 3.3:1. Preferably, feedstream 10 is preheated to about 30° C. to about 750° C., most preferably about 100° C. to about 400° C., and reactor 1 is operated at a gas hourly space velocity greater than about 50,000 hr$^{-1}$, a temperature of between about 600° C. and about 2000° C., most preferably between 600° C. and 1600° C., and a pressure between about 100 kPa and about 32,000 kPa, most preferably between about 200 kPa to about 10,000 kPa.

The reactor 1 preferably contains a catalyst comprising an active metal selected from the group of rhodium, iridium, nickel, chromium, and cobalt. Preferably, the catalyst further comprises a promoter selected from the group consisting of La, Ce, Pr, Nd, Pm, Sm, Eu, Gd, Tb, Dy, Ho, Er, Tm, Yb, Ru, and Lu.

In preferred embodiments the catalyst used for producing synthesis gas in reactor 1 comprises about 0.005 to 25 wt % Rh, preferably 0.05 to 25 wt % Rh, and about 0.005 to 25 wt % of a lanthanide element (i.e., La, Ce, Pr, Nd, Pm, Sm, Eu, Gd, Tb, Dy, Ho, Er, Tm, Yb and Lu) in the form of the metal and/or metal oxide coating a support form.

The support form can be a refractory monolith, or particulates, or a plurality of distinct or discrete structures, such as granules, beads, pills, pellets, cylinders, trilobes, extrudates, spheres or other rounded shapes, or another manufactured configuration or irregularly shaped particles. Preferably at least a majority (i.e., >50%) of the particles or distinct structures have a maximum characteristic length (i.e., longest dimension) of less than six millimeters, preferably less than three millimeters. The term "monolith" as used herein is any singular piece of material of continuous manufacture such as solid pieces of metal or metal oxide or foam materials or honeycomb structures.

In any case, the preferred Rh-Lanthanide catalyst systems or catalyst beds have sufficient porosity, or sufficiently low resistance to gas flow, to permit a stream of said reactant gas mixture to pass over the catalyst at a gas hourly space velocity (GHSV) of at least about 20,000 hr$^{-1}$, which corresponds to a weight hourly space velocity (WHSV) of about 200 hr$^{-1}$, when the reactor 1 is operated to produce synthesis gas. GHSV in reactor 1 is preferably between 50,000 and 100,000,000 hr$^{-1}$, most preferably between 100,000 and 10,000,000 hr$^{-1}$.

Preferably the catalytic partial oxidation catalyst is a rhodium-lanthanide catalyst supported on a refractory material as described in published patent application WO 02/20395. The term "refractory support" refers to any material that is mechanically stable to the high temperatures of a catalytic partial oxidation reaction, which is typically 500° C. −1,600° C., but may be as high as 2000° C. Suitable refractory support materials for the syngas catalyst include zirconia, magnesium stabilized zirconia, zirconia stabilized alumina, yttrium stabilized zirconia, calcium stabilized zirconia, alumina, modified alumina, cordierite, titania, silica, magnesia, niobia, vanadia and the like. Preferably the support comprises alumina, whether its is unmodified, stabilized or modified. Stabilizing and/or modifying can include thermally conditioning the catalyst and/or adding a modifying agent to the support. The modifying agent may comprise at least one element selected from the group consisting of aluminum, boron, silicon, gallium, selenium, rare earth metals, transition metals, alkali earth metals, and their corresponding oxides or ions.

Referring back to FIG. 1, the reactor effluent, i.e., syngas stream 20 (comprising syngas and the secondary products) is fed into separator 2 where at least a portion of the secondary products are separated from the syngas. At least a portion of one or more of the secondary products is enriched in outlet stream 50. The separated syngas stream 30 out of separator 2 mostly comprises of syngas, and can also comprise secondary products that are undesirable in outlet stream 50 and/or are not amenable to be recovered from syngas stream 20 depending on the types of separation technique used in separator 2.

Separator 2 can comprise one or more of separation techniques that are well-known in the art, such as but not limited to condensation, precipitation, absorption, adsorption, cryogenic separation, vacuum extraction, solvent extraction, filter (for example, a molecular-sieve filter or a silica-based filter), selective membrane, distillation, stripping, and the like. It should also be understood that any combination of separation techniques could be used, if desired, in order to achieve the recovery of one or more secondary products. The selection of the separation technique is largely dependent on the physical properties of the secondary product or products that are to be recovered in outlet stream 50.

Preferably, syngas stream 20 is separated by condensation into a gaseous stream, i.e., separated syngas stream 30, and a liquid stream, i.e., outlet stream 50. The temperature of syngas stream 20 which might be from about 700° C. to about 2000° C. at the exit of reactor 1 is decreased to less than 200° C. and possibly less than 100° C. The type of condenser or cooling equipment used is not of particular importance to this invention, as any suitable equipment well known in the art can be used for cooling the syngas stream 20. At least a portion of the produced secondary products present in syngas stream 20 condenses into a liquid phase to form outlet stream 50. Outlet stream 50 can also comprise some water that could be generated in reactor 1 and may be present in syngas stream 20. The separated syngas stream 30 mainly comprises syngas, but it can also contain gaseous compounds, other than CO and $H_2$, such as for example $CO_2$ and methane that are not condensed at the temperature conditions listed above.

If the produced secondary product stream is expected to contain substantial amounts of $C_1$–$C_4$ alcohols especially methanol, separator 2 may be an alcohol stripper to remove the alcohols from syngas stream 20.

If the produced secondary product stream is expected to contain substantial amounts of aromatic compounds (such as for example. benzene, toluene, or xylene), separator 2 may be a condenser, an absorption column, an extraction column, a fractionator, or a distillation column, or any other acceptable separation technique such as those listed herein or as is well known in the art to recover outlet stream 50 enriched in aromatics.

If the produced secondary product stream is expected to contain substantial amounts of $C_1$–$C_4$ acids (e.g., formic, acetic, propionic, butyric) or salts (e.g., formate, acetate, propionate, butyrate), separator 2 may be a condensation, an absorption, a precipitation, or any other acceptable separation technique such as those listed herein or as is well known in the art to recover in outlet stream 50 enriched in $C_1$–$C_4$ acids or salts.

If the produced secondary product stream is expected to contain substantial amounts of polyaromatic hydrocarbons (e.g., naphthalene, acenapthylene, fluorene), separator 2 may be a distillation column, a solvent extraction, an absorption, or any other acceptable separation technique such as those listed herein or as is well known in the art to recover outlet stream 50 enriched in polyaromatic hydrocarbons.

Referring back to FIG. 1, the separated syngas stream 30 is fed preferably to a synthesis reactor 3, in which the synthesis can be, by way of example only, Fischer-Tropsch synthesis, alcohol (particularly methanol) synthesis, hydrogen production, hydroformylation, or any other use for syngas. A typical Fischer-Tropsch reactor that could be used in synthesis reactor 3 is disclosed in Chao et al., where the separated syngas stream 30 would be converted to Fischer-Tropsch products (e.g., higher molecular-weight hydrocarbons, such as, for example, $C_{5+}$ hydrocarbons or diesel).

EXAMPLES

The following are examples of specific operating conditions and results in accordance with embodiments of the present invention.

The syngas catalysts were tested at a methane:oxygen molar ratio of 1.82:1 at gas hourly space velocities (GHSV) of about 400,000 to about 2,700,000 $hr^{-1}$, at pressures of about 45 psig to about 225 psig, respectively, and at temperature between 750° C. and 1250° C. for several days. The hydrocarbon gas (methane) was pre-heated and then mixed with $O_2$ so that the average temperature of the feedstream reaches a temperature around 200–300° C. before it contacts the catalyst. The catalytic partial oxidation reaction was carried out in a conventional flow apparatus using a 12.7 mm I.D. quartz insert embedded inside a refractory-lined steel vessel. The quartz insert contained a catalyst bed (2 g –5 g) containing a 9.5 mm to 30 mm catalyst bed held between two inert 80-ppi alumina foams. The effluent steam from the reactor was cooled to about 15° C. –20° C., to recover a liquid phase and a gas phase. The products were analyzed using standard gas, ion, and liquid chromatography techniques as are well known in the art. The following Table 1 indicates the amount of secondary products produced in various reactors under the listed conditions in accordance with embodiments of the present invention. Particularly, the aromatics were shown using 4% Rh–4% Sm on alumina at 45–90 psig.

TABLE 1

| Catalyst | P (psig) | Secondary Product | Concentration |
| --- | --- | --- | --- |
| 4% Rh—4% Sm | 45 psig | MeOH | ≈9000 µg/ml |
| | | Aromatics (e.g., benzene, toluene, zylene) | ≈500 µg/ml |
| | | $C_1$–$C_4$ acids (e.g., formate, acetate, propionate, butyrate) | ≈7300 µg/ml |
| | | Polyaromatic hydrocarbons (e.g., naphthalene, acenapthylene, fluorene) | ≈100 mg/L |

Shown in Table 2, is an example of the expected yields of various products using the reaction conditions of the embodiments listed above. The yields shown in Table 2 are merely examples of yields observed under certain conditions. Yields may indeed be higher or lower depending on reaction conditions and separation techniques. By way of example only, the yield of methanol may be as high as 70 mg/g, benzene may be as high as $4.4 \times 10^{-3}$ mg/g, acetic acid as high as 3 mg/g, and formate as high as 60 mg/g.

TABLE 2

| Compound | Yield (mg/g hydrocarbon feed) |
| --- | --- |
| Methanol | 0.13 – 7.31 |
| Benzene | $4.4 \times 10^{-5}$ – $2.2 \times 10^{-5}$ |
| Toluene | $<4.4 \times 10^{-5}$ |
| Xylene | $<1.1 \times 10^{-5}$ |
| Naphthalene | $2.6 \times 10^{-4}$ – 0.025 |
| Acenaphthylene | $2.0 \times 10^{-3}$ – 0.056 |
| Flourene | $5.49 \times 10^{-5}$ – $3.2 \times 10^{-3}$ |
| Formic Acid/Formate | $5.9 \times 10^{-4}$ – 5.7 |
| Acetic Acid/Acetate | $1.3 \times 10^{-3}$ – 0.23 |
| $C_3$ Acid/Propionate | $<2.2 \times 10^{-4}$ – $3.2 \times 10^{-3}$ |
| $C_4$ Acid/Butyrate | $<8.1 \times 10^{-4}$ |

It would be evident to one of ordinary skill in the art, that for the preferred embodiment with the use of condensation in separator 2, one limit on the amount of secondary product(s) recovered from the reactor effluent stream is the solubility limit of the secondary product(s) in the liquid phase obtained in outlet stream 50 which should contain most of the water generated during the syngas reaction. The solubility of a given secondary product may be dependent on the conditions (e.g., temperature and pressure) under which stream 50 is maintained.

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The disclosures of all issued patents, patent applications and publications cited herein are incorporated by reference. Should the disclosure of any of the patents and publications that are incorporated herein by reference conflict with the present specification to the extent that it might render a term unclear, the present specification shall take precedence.

What is claimed is:

1. A method for producing at least one secondary product and syngas from a feedstream comprising a gaseous hydrocarbon and oxygen, the method comprising:
   reacting the feedstream in a reactor configured to partially oxidize at least a portion of the gaseous hydrocarbon to syngas and to produce the at least one secondary product; and
   separating at least a portion of the at least one secondary product from the syngas;
   wherein the at least one secondary product is selected from the group consisting of $C_1$–$C_4$ alcohols, aromatics, $C_1$–$C_4$ acids, and poly-aromatic compounds.

2. The method of claim 1 wherein the secondary products comprise $C_1$–$C_4$ alcohols.

3. The method of claim 2 wherein the secondary products comprises less than about 70 mg methanol per gram of gaseous hydrocarbon feed.

4. The method of claim 3 wherein the separating step is conducted in an alcohol stripper.

5. The method of claim 1 wherein the secondary products comprise aromatics.

6. The method of claim 5 wherein the secondary products comprise less than about $4.4 \times 10^{-3}$ mg benzene per gram of gaseous hydrocarbon feed.

7. The method of claim 5 wherein the secondary products comprise less than about 0.44 mg xylene per gram of gaseous hydrocarbon feed.

8. The method of claim 1 wherein the secondary product comprises $C_1$–$C_4$ acids.

9. The method of claim 8 wherein the secondary product comprises less than about 3 mg acetic acid per gram of gaseous hydrocarbon feed.

10. The method of claim 8 wherein the secondary product comprises less than about 60 mg formate per gram of gaseous hydrocarbon feed.

11. The method of claim 1 wherein the secondary product comprises a poly-aromatic-hydrocarbon.

12. The method of claim 1 wherein the feedstream flows through the reactor at a gas hourly space velocity of greater than about 20,000 $hr^{-1}$.

13. The method of claim 1 wherein the reactor contains a catalyst comprising an active metal selected from the group of rhodium, iridium, nickel, chromium, cobalt.

14. The method of claim 13 wherein the catalyst comprises rhodium.

15. The method of claim 13 wherein the catalyst further comprises a promoter selected from the group consisting of La, Ce, Pr, Nd, Pm, Sm, Eu, Gd, Tb, Dy, Ho, Er, Tm, Yb, Ru and Lu.

16. The method of claim 15 wherein the catalyst comprises a lanthanide element selected from the group consisting of La, Ce, Sm, and Yb.

17. The method of claim 13 wherein the lanthanide element comprises about 0.005 wt % to 25 wt % of the catalyst.

18. The method of claim 1 wherein the separating step comprises a method selected from the group consisting of condensation, precipitation, absorption, adsorption, cryogenic separation, vacuum extraction, solvent extraction, filtration, selective membrane separation, distillation, stripping, and any combination thereof.

19. The method of claim 1 wherein the separating step comprises cooling the secondary product and syngas stream to no more than about 200° C.

* * * * *